United States Patent
Kaethner et al.

(10) Patent No.: US 11,823,387 B2
(45) Date of Patent: Nov. 21, 2023

(54) PROVIDING A VASCULAR IMAGE DATA RECORD

(71) Applicant: Siemens Healthcare GmbH, Erlangen (DE)

(72) Inventors: Christian Kaethner, Forchheim (DE); Julie DiNitto, Memphis, TN (US); Annette Birkhold, Nuremberg (DE); Michael Manhart, Fürth (DE); Markus Kowarschik, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 303 days.

(21) Appl. No.: 17/110,270

(22) Filed: Dec. 2, 2020

(65) Prior Publication Data

US 2021/0166392 A1 Jun. 3, 2021

(30) Foreign Application Priority Data

Dec. 3, 2019 (DE) ...................... 10 2019 218 770.6

(51) Int. Cl.
*A61B 6/00* (2006.01)
*A61B 6/12* (2006.01)
(Continued)

(52) U.S. Cl.
CPC ............ *G06T 7/0016* (2013.01); *A61B 6/481* (2013.01); *A61B 6/504* (2013.01); *G06N 3/08* (2013.01);
(Continued)

(58) Field of Classification Search
None
See application file for complete search history.

(56) References Cited

U.S. PATENT DOCUMENTS 9,833,211 B2 * 12/2017 Nagae .................... A61B 6/486
10,653,379 B2 * 5/2020 Rapoport ............... G16H 50/30
(Continued)

FOREIGN PATENT DOCUMENTS

DE 102010041443 A1 3/2012
DE 102014213408 A1 1/2016

OTHER PUBLICATIONS

German Office Action for German Application No. 10 2019 218 770.6 dated Aug. 5, 2020.

*Primary Examiner* — Soo Shin
(74) *Attorney, Agent, or Firm* — Lempia Summerfield Katz LLC

(57) ABSTRACT

A computer-implemented method for providing a vascular image data record includes receiving a plurality of projection-X-ray images recorded in temporal succession. The plurality of projection-X-ray images at least partially map a common examination region of an examination object. The plurality of projection-X-ray images map a temporal change in the examination region of the examination object. A change image data record is determined in each case based on at least one region of interest of the plurality of projection-X-ray images. The at least one region of interest includes a plurality of image points. The change image data record in each case includes a time-intensity curve for each of the image points. The vascular image data record is generated based on the change image data record, and the vascular image data record is provided.

12 Claims, 9 Drawing Sheets

(51) Int. Cl.
*G06T 7/00* (2017.01)
*G16H 30/20* (2018.01)
*G16H 30/40* (2018.01)
*G16H 50/50* (2018.01)
*G16H 50/70* (2018.01)
*G16H 50/20* (2018.01)
*G06N 3/08* (2023.01)
*G06N 3/04* (2023.01)
*G16H 40/67* (2018.01)

(52) U.S. Cl.
CPC ............. *G16H 30/20* (2018.01); *G16H 30/40* (2018.01); *G16H 50/20* (2018.01); *G16H 50/50* (2018.01); *G16H 50/70* (2018.01); *G06N 3/04* (2013.01); *G06T 2207/10116* (2013.01); *G06T 2207/20081* (2013.01); *G06T 2207/30101* (2013.01); *G16H 40/67* (2018.01)

(56) References Cited

U.S. PATENT DOCUMENTS

| | | | | |
|---|---|---|---|---|
| 11,532,074 | B2* | 12/2022 | Kaethner | G06N 20/00 |
| 2009/0016587 | A1* | 1/2009 | Strobel | G06T 7/20 |
| | | | | 382/130 |
| 2009/0028409 | A1* | 1/2009 | Tsukagoshi | A61B 6/032 |
| | | | | 378/15 |
| 2009/0046914 | A1* | 2/2009 | Khazen | G06T 15/08 |
| | | | | 382/131 |
| 2011/0235885 | A1* | 9/2011 | Rauch | A61B 6/481 |
| | | | | 382/131 |
| 2015/0173699 | A1* | 6/2015 | Kyriakou | A61B 6/466 |
| | | | | 378/62 |
| 2016/0012636 | A1* | 1/2016 | Lauritsch | A61B 6/5294 |
| | | | | 345/420 |
| 2016/0350913 | A1* | 12/2016 | Nagae | G06T 7/174 |
| 2017/0265829 | A1* | 9/2017 | Adam | A61B 6/504 |
| 2018/0350080 | A1* | 12/2018 | Kao | A61B 6/5211 |
| 2019/0365336 | A1* | 12/2019 | Wagner | G16H 50/30 |
| 2020/0013153 | A1* | 1/2020 | Kaethner | G06T 5/50 |
| 2022/0051401 | A1* | 2/2022 | Lenich | A61B 6/504 |
| 2022/0125398 | A1* | 4/2022 | Aben | A61B 8/0883 |

* cited by examiner

PROVIDING A VASCULAR IMAGE DATA RECORD

This application claims the benefit of German Patent Application No. DE 10 2019 218 770.6, filed on Dec. 3, 2019, which is hereby incorporated by reference in its entirety.

BACKGROUND

The present embodiments relate to a computer-implemented method for providing a vascular image data record, a computer-implemented method for providing a trained function, a providing unit, a training unit, a medical X-ray device, a computer program product, and a computer-readable storage medium.

X-ray based imaging methods are frequently used to detect temporal changes to an examination region of an examination object (e.g., a human and/or animal patient). Herein, the temporal change to the examination region of the examination object may include, for example, a propagation movement and/or flow movement of a contrast agent in a vascular system and/or a movement of a medical object (e.g., a medical instrument, such as a catheter and/or guide wire) and/or a diagnostic instrument (e.g., an endoscope).

X-ray based imaging methods frequently include digital subtraction angiography (DSA), where at least two X-ray images recorded in temporal succession, which at least partially map the common examination region, are subtracted from one another. Herein, one of the at least two X-ray images is frequently a mask image, which was recorded in a mask phase of the DSA. Further, the at least one further X-ray image may frequently be recorded in a filling phase of the DSA. Frequently, a differential image is provided as a result of the DSA. This frequently enables components of the differential image that are irrelevant or disruptive with respect to treatment and/or diagnosis, which are, for example, temporally invariant, to be reduced and/or removed.

Herein, one frequent drawback is that two different phases of the recording of the X-ray images, the mask phase and the filling phase, are to be provided to map a vessel section in the examination region of the examination object. For example, in the case of 3D DSA, this frequently results in increased expenditure of time and a higher X-ray dose for the examination object.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method for providing a vascular image data record that is particularly efficient with respect to time and X-ray dose is provided.

Methods and apparatuses for providing a vascular image data record and methods and apparatuses for providing a trained function are provided. Herein, features, advantages, and alternative embodiments of data structures and/or functions with methods and apparatuses for providing a vascular image data record may be transferred to similar data structures and/or functions with methods and apparatuses for providing a trained function. Herein, similar data structures may, for example, be characterized by the use of the prefix "training". Further, the trained functions used in methods and apparatuses for providing a vascular image data record may, for example, have been adjusted or provided by methods and apparatuses for providing a trained function.

In a first aspect, the present embodiments relate to a computer-implemented method for providing a vascular image data record. Herein, in act a), a plurality of projection-X-ray images recorded in temporal succession are received. Herein, the plurality of projection-X-ray images at least partially map a common examination region of an examination object. Further, the plurality of projection-X-ray images map a temporal change in the examination region of the examination object. In act b), a change image data record is determined in each case based on at least one region of interest of the plurality of projection-X-ray images. Herein, the at least one region of interest includes a plurality of image points. Further, the change image data record in each case includes a time-intensity curve for each of the image points. In act c), the vascular image data record is generated based on the change image data record. In act d), the vascular image data record is provided.

The reception of the plurality of projection-X-ray images recorded in temporal succession may, for example, include detection and/or reading-out of a computer-readable data memory and/or reception from a data memory unit (e.g., a database). Further, a plurality of projection-X-ray images recorded in temporal succession may be provided by a providing unit of a medical X-ray device.

Further, the plurality of projection-X-ray images may include a plurality of image points (e.g., pixels and/or voxels). In one embodiment, the plurality of projection-X-ray images at least partially map the common examination region of the examination object. Herein, each projection X-ray image of the plurality of projection-X-ray images may in each case include a two-dimensional projection mapping of the common examination region of the examination object. In one embodiment, the plurality of projection-X-ray images may be recorded from different projection directions (e.g., angulations) relative to the examination region of the examination object.

In addition, the plurality of projection-X-ray images may map a temporal change (e.g., a propagation movement and/or flow movement of a contrast agent in a vascular system of the examination object and/or a movement of a medical object, such as a guide wire and/or a catheter and/or an endoscope and/or of laparoscope) in the examination region of the examination object.

Further, the examination region of the examination object may include a vessel section and/or a section of a vascular tree to be mapped. In one embodiment, the vessel section and/or vascular tree section to be mapped may be mapped in the at least one region of interest of the plurality of projection-X-ray images. Further, the plurality of projection-X-ray images may map the temporal change within the vessel section to be mapped and/or within the vascular tree section to be mapped (e.g., completely). For example, a propagation movement and/or flow movement of a contrast agent may be mapped up to filling and/or up to passage through the vessel section to be mapped and/or the vascular tree section to be mapped as the temporal change in the plurality of projection-X-ray images. Further, a movement of a medical object may be mapped from a starting position up to a target position in the plurality of projection-X-ray images.

In act b), the change image data record may be determined in each case based on at least one region of interest (ROI) of the plurality of projection-X-ray images. Herein, the at least one region of interest may be specified with reference to an anatomical feature (e.g., the vessel section to be mapped and/or the vascular tree section to be mapped). Further, the at least one region of interest may in each case include a plurality of image points in the plurality of projection-X-ray images. Herein, a circumference and/or an extension of the at least one region of interest of the plurality of projection-X-ray images may be dependent on the mapping of the vessel section to be mapped and/or the vascular tree section to be mapped contained therein.

For example, the at least one region of interest of the plurality of projection-X-ray images may in each case include different image points that correspond to the same examination region of the examination object to be mapped. In one embodiment, the determination of the change image data record may be based on the mutually corresponding image points of the at least one region of interest of the plurality of projection-X-ray images. Herein, the mutually corresponding image points may in each case map the same examination region of the examination object in the plurality of projection-X-ray images.

Further, the plurality of projection-X-ray images may be recorded such that the plurality of projection-X-ray images map the examination region of the examination object from the projection directions of a plurality of rotations (e.g., complete rotations) about the examination object. Herein, the change image data record may be based on the at least one region of interest of the projection-X-ray images with mutually corresponding projection directions from the different rotations (e.g., rotational runs).

In one embodiment, the change image data record for each of the image points of the at least one region of interest may in each case include a time-intensity curve. Herein, each of the image points may in each case include an intensity value (e.g., a gray value and/or RGB value). The time-intensity curve includes the intensity values of the respective image point over the recording time points of the plurality of projection-X-ray images. Herein, the determination of the change image data record (e.g., the time-intensity curves for each of the image points) may include interpolation and/or extrapolation. The change image data record may be three-dimensional and/or four-dimensional. Herein, the change image data record may map the image points of the at least one region of interest (e.g., three-dimensionally) and include the temporal change in the intensity values of the image points in the fourth dimension.

In act c), the vascular image data record may be generated based on the change image data record. Herein, the vascular image data record may, for example, include two-dimensional and/or three-dimensional mapping of the vessel section to be mapped and/or the vascular tree section to be mapped from the examination region of the examination object. Further, the vascular image data record may include an additional dimension for mapping a flow in the vessel section and/or vascular tree section mapped therein.

Further, the vascular image data record may include a two-dimensional and/or three-dimensional vascular model. Herein, the vascular model may include a center line and/or geometric and/or physiological information (e.g., a diameter) and/or a flow parameter, relating to the mapped vessel section and/or vascular tree section.

Herein, the generation of the vascular image data record may, for example, include segmentation and/or masking of the image points of the at least one region of interest based on the time-intensity curves of the change image data record. Herein, the image points mapping the vessel section and/or the vascular tree section may be classified. Further, the vascular model (e.g., the physiological information) may be determined based on the time-intensity curves of the image points mapping the vessel section and/or the vascular tree section.

Further, the provision of the vascular image data record may, for example, include storage on a computer-readable storage medium and/or displaying on a display unit and/or transmission to a providing unit.

Herein, in contrast to the known DSA method, a mask phase may be dispensed with, where the vascular image data record is generated based on the information contained in the plurality of projection-X-ray images from the filling phase. This may achieve both a saving of time and a reduction of X-ray dose for the examination object.

In a further embodiment of the computer-implemented method for providing a vascular image data record, the vascular image data record may be generated based on a threshold value with respect to the time-intensity curves of the change image data record.

Herein, the threshold value may, for example, include a minimum intensity value, where the minimum intensity value relates to an image contrast corresponding to a mapping of the vessel section and/or the vascular tree section. Herein, the threshold value may be specified in dependence on a recording parameter and/or an operating parameter of the medical X-ray device for the recording of the plurality of projection-X-ray images. Further, the threshold value may be specified in dependence on a contrast agent dose and/or an injection rate of a contrast agent and/or a physiological parameter of the examination object and/or an operating parameter of a medical object located in the examination region. In addition, the threshold value may be specified based on the anatomical region of the examination object mapped in the at least one region of interest.

Herein, the generation of the vascular image data record may take place based on a comparison of the time-intensity curves of the change image data record with the threshold value. For example, the image points of the change image data record that include a time-intensity curve with at least one intensity value above the specified threshold value may be classified in order to generate the vascular image data record.

This may provide that the image points of the change date record with a time-intensity curve with an intensity value above the specified threshold value are classified such that the image points are taken into account during the generation of the vascular image data record as mapping of the vessel section and/or the vascular tree section.

In a further embodiment of the computer-implemented method for providing a vascular image data record, in each case, a temporal variance may be determined for each time-intensity curve of the change image data record. Further, the generation of the vascular image data record in act c) may include segmentation of the image points based on a comparison of the variance with the threshold value.

Herein, the threshold value can specify a minimum temporal change (e.g., a minimum temporal variance) with respect to the time-intensity curves of the image points of the change image data record. For example, the threshold value may specify a temporal variance with respect to the time-intensity curves of the image points of the change image data record averaged over a specific period of time. Herein, the specific period of time may be specified in dependence on an operating parameter and/or recording parameter of the X-ray device, and/or in dependence on an injection rate of the contrast agent, and/or in dependence on a physiological parameter of the examination object, and/or in dependence on an operating parameter of a medical object located in the examination region.

Further, a temporal variance (e.g., averaged over the specific period of time) may be determined for each of the time-intensity curves, where the associated image point is classified based on a comparison of this temporal variance with the threshold value. Herein, the temporal variance may, for example, include information on the distribution of the intensity values in the specific period of time. Further, the variance may include an interval of a minimum and a maximum intensity value of the time-intensity curve of the respective image point within the specific time section. This may enable particularly robust generation of the vascular image data record with respect to image artifacts and/or motion artifacts.

In a further embodiment of the computer-implemented method for providing a vascular image data record, a temporal maximum intensity projection (TMIP) may be generated based on the plurality of projection-X-ray images. Herein, the vascular image data record may additionally be generated based on the temporal maximum intensity projection.

Herein, a four-dimensional intermediate data record and/or at least two three-dimensional intermediate data records may be reconstructed based on the plurality of projection-X-ray images. For example, in each case, a three-dimensional intermediate data record may be reconstructed to form the projection-X-ray images of a rotation (e.g., a rotation run) of the recording of the plurality of projection-X-ray images. Following this, the three-dimensional intermediate data records may be combined according to the recording time points of the respective projection-X-ray images to form the four-dimensional intermediate data record.

Herein, the temporal maximum intensity projection may, for example, include a projection of at least one three-dimensional intermediate data record in each case along a predetermined projection direction. On the generation of the temporal maximum intensity projection, it is possible in each case to determine along the predetermined projection direction an image point of the at least two three-dimensional intermediate data records and/or the four-dimensional intermediate data record corresponding to an image point of the temporal maximum intensity projection. Herein, the image point determined may include a maximum intensity value (e.g., a maximum sum of intensity values) along the temporal dimension of the recording time points assigned to the at least two intermediate data records and/or along the fourth dimension of the four-dimensional intermediate data record.

Additionally taking account of the temporal maximum intensity projection on the generation of the vascular image data record in act c) enables the robustness of the segmentation and/or masking of the vessel section to be mapped and/or the vascular tree section to be mapped to be improved.

In a further embodiment of the computer-implemented method for providing a vascular image data record, the generation of the vascular image data record may be performed by applying a trained function to input data. Herein, the input data may be based on the change image data record. Further, at least one parameter of the trained function may be based on a comparison of a training vascular image data record and a comparison image data record.

The trained function may be trained by a machine learning method. For example, the trained function may be a neural network (e.g., a convolutional neural network (CNN) or a network comprising a convolutional layer).

The trained function maps input data on output data. Herein, the output data may, for example, also depend on one or more parameters of the trained function. The one or more parameters of the trained function may be determined and/or adjusted by training. The determination and/or adjustment of the one or more parameters of the trained function may, for example, be based on a pair consisting of training input data and associated training output data, where the trained function is applied to the training input data in order to generate training mapping data. For example, the determination and/or the adjustment may be based on a comparison of the training mapping data and the training output data. Generally, a trainable function (e.g., a function with one or more parameters that have not yet been adjusted) is also referred to as a trained function.

Other terms for trained function are trained mapping rule, mapping rule with trained parameters, function with trained parameters, algorithm based on artificial intelligence, machine learning algorithm. One example of a trained function is an artificial neural network, where the edge weights of the artificial neural network correspond to the parameters of the trained function. Instead of the term "neural network", it is also possible to use the term "neural net". For example, a trained function may also be a deep neural network or deep artificial neural network. A further example of a trained function is a "support vector machine"; further, it is also possible, for example, to use other machine learning algorithms as a trained function.

The trained function may, for example, be trained by backpropagation. Initially, training mapping data may be determined by applying the trained function to training input data. After this, a deviation between the training mapping data and the training output data may be ascertained by applying an error function to the training mapping data and the training output data. Further, at least one parameter (e.g., a weighting) of the trained function (e.g., of the neural network) may be iteratively adjusted based on a gradient of the error function with respect to the at least one parameter of the trained function. This enables the deviation between the training mapping data and the training output data during the training of the trained function to be minimized.

In one embodiment, the trained function (e.g., the neural network) includes an input layer and an output layer. Herein, the input layer may be embodied to receive input data. Further, the output layer may be embodied to provide mapping data. Herein, the input layer and/or the output layer may in each case include a plurality of channels (e.g., neurons).

In one embodiment, at least one parameter of the trained function may be based on a comparison of a training vascular image data record with a comparison vascular image data record. Herein, the training vascular image data record and/or the comparison vascular image data record may be determined as part of a suggested computer-implemented method for providing a trained function; this will be explained in the further course of the description. For example, the trained function may be provided by an embodiment of the suggested computer-implemented method for providing a trained function.

This enables all information contained in the time-intensity curves of the change image data record (e.g., information relevant for the generation of the vascular image data record) to be processed by the trained function.

In a further embodiment of the computer-implemented method for providing a vascular image data record, the trained function input data may also be based on the temporal maximum intensity projection.

This may improve robustness of the generation of the vascular image data record by the application of the trained function to the input data.

In a further embodiment of the computer-implemented method for providing a vascular image data record, the plurality of projection-X-ray images may map different temporally sequential phases of the temporal change in the examination region of the examination object. Herein, act b) may include a determination in each case of a phase-change image data record for each of the phases of the temporal change. Further, in act c), the vascular image data record may be generated based on the phase-change image data records.

Herein, the different temporally sequential phases of the temporal change in the examination region of the examination object may be specified based on a physiological parameter of the examination object and/or based on an operating parameter and/or recording parameter of the medical X-ray device for recording the plurality of projection-X-ray images and/or based on an injection rate of a contrast agent and/or based on an operating parameter of a medical object located in the examination region.

Herein, the phases of the temporal change in the examination region of the examination object may, for example, in each case, include a temporally and spatially limited location of a contrast agent in the vessel section to be mapped and/or the vascular tree section to be mapped. For example, the phases of the temporal change may be specified with reference to the injection rate of the contrast agent and/or with reference to the operating parameter and/or the recording parameter of the medical X-ray device such that, in each phase, the contrast agent is in each case located in another (e.g., adjacent) subsection of the vessel section to be mapped and/or the vascular tree section to be mapped. This enables complete filling of the vessel section to be mapped and/or the vascular tree section to be mapped with the contrast agent to be dispensed with. Hence, it may be sufficient for a temporally and spatially limited contrast agent bolus to flow through the examination region of the examination object during the recording of the plurality of projection-X-ray images. Herein, the temporal change may be divided between the temporally sequential phases such that each of the phases corresponds to a different location of the contrast agent bolus in the examination region of the examination object from that in the previous phase.

Further, the phases of the temporal change may be specified such that each of the temporally sequential phases corresponds to a location of the medical object in the vessel section to be mapped and/or in the vascular tree section to be mapped that has changed compared to that in the previous phase.

For example, the plurality of projection-X-ray images may be recorded such that the phases of the temporal change in the examination region of the examination object are in each case mapped by a subset of the plurality of projection-X-ray images corresponding to a rotation (e.g., a rotation run).

In act b), it is possible for a phase-change image data record to be determined for each of the temporally sequential phases of the temporal change. Herein, the phase-change image data records may (e.g., similarly to the change image data record) be determined in each case based on at least one region of interest of the projection-X-ray images corresponding to the respective phase. For example, in each case, one of the phase-change image data records may be determined based on the at least one region of interest of the subset of the plurality of projection-X-ray images corresponding to the respective phase. Herein, the at least one region of interest may include a plurality of image points of the respective subset of the plurality of projection-X-ray images. Further, each of the phase-change image data records may include the image points of the at least one region of interest. In addition, each of the phase-change image data records for each of the image points may in each case include a time-intensity curve. The time-intensity curves may include the intensity values of the respective image point over the recording time points of the respective subset of the plurality of projection-X-ray images. For example, each phase-change image data record may include the time-intensity curves for the period of time of the recording time points of the plurality of projection-X-ray images corresponding to the temporal phase.

In act c), the vascular image data record may be generated based on the phase-change image data records. For this, in each case, a subsection of the vessel section to be mapped and/or the vascular tree section to be mapped may be segmented and/or masked in the phase-change image data records based on the time-intensity curves. Superimposition and/or addition and/or multiplication (e.g., weighted) of the vascular image data record may be generated based on the phase-change image data records (e.g., the subsections of the vessel section to be mapped and/or the vascular tree section to be mapped) that are segmented and/or masked therefrom.

This enables particularly accurate and computationally efficient generation of the vascular image data record. Further, the time expenditure, the X-ray dose, and the contrast agent dose for recording the plurality of projection-X-ray images may be reduced by the specification of the temporally sequential phases of the temporal change in the examination region.

In a further embodiment of the computer-implemented method for providing a vascular image data record, the phase-change image data records for each of the image points may in each case include a time-intensity curve. Herein, the vascular image data record may be completed based on a threshold value with respect to the time-intensity curves of the phase-change image data records.

Herein, the threshold value may, for example, include a minimum intensity value, where the minimum intensity value relates to an image contrast corresponding to a mapping of the vessel section and/or the vascular tree section. Further, the threshold value may specify a minimum temporal change (e.g., a minimum temporal variance) with respect to the time-intensity curves of the image points of the respective change image data record. For example, the threshold value may specify a temporal variance with respect to the time-intensity curves of the image points of the respective change image data record averaged over a specific period of time. Herein, the specific period of time may be specified in dependence on an operating parameter and/or recording parameter of the X-ray device and/or in dependence on an injection rate of the contrast agent and/or in dependence on a physiological parameter of the examination object and/or in dependence on an operating parameter of a medical object arranged the examination region.

Herein, the completion of the vascular image data record may take place step-by-step. Herein, in a first act, the image points of a first phase-change image data record may be classified based on the threshold value with respect to the time-intensity curves of the first phase-change image data record.

The classification of the image points of the first phase-change image data record may, for example, be based on a comparison of the time-intensity curves of the change image data record with the threshold value. For example, the image points of the first change image data record that include a time-intensity curve with at least one intensity value above the specified threshold value may be classified as image points mapping the vessel section and/or the vascular tree section.

Further, a temporal variance (e.g., averaged over the specific period of time) may be determined for each of the time-intensity curves. The associated image point is classified based on a comparison of this temporal variance with the threshold value. Herein, the temporal variance may, for example, include information on a distribution of the intensity values in the specific period of time. Further, the variance may include an interval of a minimum and a maximum intensity value of the time-intensity curve of the respective image point within the specific time section.

In one embodiment, the classification of the image points of the further phase-change image data records in the further acts of the completion of the vascular image data record may take place similarly to the classification of the image points of the first phase-change image data record based on the threshold value with respect to the time-intensity curves of the respective phase-change image data record. Herein, the image points classified in the first act as mapping the vessel section and/or the vascular tree section may be taken into account in the further acts of the completion of the vascular image data record and/or excluded from the further classification. Herein, the vascular image data record may include all image points classified as mapping the vessel section and/or the vascular tree section in the acts of the completion. This may enable particularly computationally efficient generation of the vascular image data record.

In a further embodiment of the computer-implemented method for providing a vascular image data record, the completion of the vascular image data records may take place step-by-step based on the phase-change image data records. Herein, image points may be classified with reference to the threshold value with respect to the time-intensity curves of the respective phase-change image data record in each step of the completion of the vascular image data record. Herein, the classification of the image points may take place based on the image points that have already been classified previously.

Herein, the classification of the image points may begin in an environment (e.g., in adjacent image points) of image points classified as mapping the vessel section and/or the vascular tree section. Herein, it is, for example, also possible to take account of anatomical and/or geometric information (e.g., probability information) relating to a course of the vessel section to be mapped and/or the vascular tree section to be mapped during the step-by-step classification of the image points based on the image points that have already been classified. For example, it is possible for a direction and/or a region of image points to be specified for the particularly computationally efficient classification of the image points in the further phase-change image data records based on the anatomical and/or geometric information.

In a further embodiment of the computer-implemented method for providing a vascular image data record, the temporal change in the examination region of the examination object may be caused by a contrast agent bolus.

Herein, the contrast agent bolus may describe a temporally and spatially limited contrast agent flow in the examination region of the examination object. For example, the contrast agent bolus may flow through the examination region of the examination object during the recording of the plurality of projection-X-ray images.

For example, the plurality of projection-X-ray images may be recorded such that the temporal course of a contrast agent bolus, which in each case, in one projection-X-ray image of the plurality of projection-X-ray images only flows through a spatial subregion of the vessel section to be mapped and/or the vascular tree section to be mapped, is completely mapped in the plurality of projection-X-ray images.

Herein, in contrast to the known DSA methods, a mask phase may be omitted, where the vascular image data record may be generated based on the contrast agent bolus for which the temporal course of a flow is mapped in the plurality of projection-X-ray images. This may enable time to be saved and the X-ray dose for the examination object to be reduced.

In a second aspect, the present embodiments relate to a computer-implemented method for providing a trained function. Herein, in a first act, a plurality of training projection X-ray images recorded in temporal succession are received. Herein, the plurality of training projection X-ray images at least partially map a common examination region of an examination object. Further, the plurality of training projection X-ray images map a temporal change in the examination region of the examination object. In a second act, a training change image data record is determined in each case based on at least one training region of interest of the plurality of training projection X-ray images. Herein, the at least one training region of interest includes a plurality of training image points. In addition, the training change image data record for each of the training image points in each case includes a training time-intensity curve. In a fourth act, a comparison vascular image data record is generated based on the training change image data record. In a fifth act, a training vascular image data record is generating by applying the trained function to input data. Herein, the input data is based on the training change image data record. In a sixth act, at least one parameter of the trained function is adjusted based on a comparison of the comparison vascular image data record and the training vascular image data record. After this, the trained function is provided.

The reception of the plurality of training projection X-ray images recorded in temporal succession may, for example, include detection and/or reading-out of a computer-readable data memory and/or a reception from a data memory unit (e.g., a database). Further, a plurality of training projection X-ray images recorded in temporal succession may be provided by a providing unit of a medical X-ray device.

The plurality of training projection X-ray images may, for example, include all the properties of the plurality of projection-X-ray images that were described with respect to the computer-implemented method for providing a vascular image data record and vice versa. For example, the training projection X-ray images may be projection-X-ray images. Further, the training projection X-ray images may be simulated.

Further, the plurality of training projection X-ray images may include a plurality of image points (e.g., pixels and/or voxels). In one embodiment, the plurality of training projection X-ray images at least partially map the common examination region of the examination object. Herein, each training projection X-ray image of the plurality of training projection X-ray images may in each case include two-dimensional projection mapping of the common examination region of the examination object. In one embodiment, the plurality of training projection X-ray images may be recorded from different projection directions (e.g., angulations) relative to the examination region of the examination object.

In addition, the plurality of training projection X-ray images may map a temporal change (e.g., a propagation movement and/or flow movement of a contrast agent in a vascular system of the examination object and/or a movement of a medical object, such as a guide wire and/or a catheter and/or an endoscope and/or a laparoscope) in the examination region of the examination object.

The training change image data record may be determined based on the, in each case, at least one region of interest of the plurality of training projection X-ray images. Herein, the at least one training region of interest may be specified with reference to an anatomical feature (e.g., the vessel section to be mapped and/or the vascular tree section to be mapped). Further, the at least one training region of interest may in each case include a plurality of training image points of the plurality of training projection X-ray images. Herein, a circumference and/or an extension of the at least one training region of interest of the plurality of training projection X-ray images may be dependent on the mapping of the vessel section to be mapped and/or the vascular tree section to be mapped contained therein.

For example, the at least one training region of interest of the plurality of training projection X-ray images may, in each case, include different training image points that correspond to the same examination region of the examination object to be mapped. In one embodiment, the determination of the training change image data record may be based on the mutually corresponding training image points of the at least one training region of interest of the plurality of training projection X-ray images. Herein, the mutually corresponding training image points may, in each case, map the same examination region of the examination object of the plurality of training projection X-ray images.

Further, the plurality of training projection X-ray images may be recorded such that the plurality of training projection X-ray images map the examination region of the examination object from projection directions of a plurality of rotations (e.g., complete rotations) about the examination object. Herein, the training change image data record may be based on the at least one region of interest of the training projection X-ray images with mutually corresponding projection directions from the different rotations (e.g., rotation runs).

In one embodiment, the training change image data record for each of the training image points of the at least one training region of interest may in each case include a training time-intensity curve. Herein, each of the training image points may, in each case, include an intensity value (e.g., a gray value and/or RGB value). The training time-intensity curve includes the intensity values of the respective training image point over the recording time points of the plurality of training projection X-ray images. Herein, the determination of the training change image data record (e.g., the training time-intensity curves for each of the training image points may include interpolation and/or extrapolation). The training change image data record may be three-dimensional and/or four-dimensional. Herein, the training change image data record may map the training image points of the at least one training region of interest (e.g., three-dimensionally) and includes the temporal change in the intensity values of the training image points in the fourth dimension.

According to one embodiment of the suggested method for providing a vascular image data record, the comparison vascular image data record is generated based on a threshold value with respect to the training time-intensity curves of the training change image data record. Herein, the training change image data record including the training time-intensity curves may be provided as a change image data record including the time-intensity curves. Further, the comparison vascular image data record may be generated by manual and/or semiautomatic annotation of the change image data record.

Further, the plurality of training projection X-ray images may be simulated based on a vascular model. Herein, the comparison vascular image data record may additionally be generated based on the vascular model underlying the simulation.

The training vascular image data record may be generated by applying the trained function to the input data based on the training change image data record.

Further, at least one parameter of the trained function may be adjusted based on the comparison of the training vascular image data record and the comparison image data record. Herein, the comparison may, for example, a difference and/or a scalar product and/or take place based on geometric and/or anatomical features.

This enables the generation of the vascular image data record to be improved by applying the trained function to the input data. For example, image points of the change date record that cannot be classified directly with reference to the change image data record (e.g., with reference to the time-intensity curves) as image points mapping the vessel section and/or the vascular tree section may be reliably classified by applying the trained function. Herein, the trained function may, for example, complete and/or correct gaps and/or artifacts in the change image data record between anatomically coherent structures during the generation of the vascular image data record.

The provision of the trained function may, for example, include storage on a computer-readable storage medium and/or transmission to a providing unit.

In one embodiment, the suggested method may provide a trained function, which may be used in an embodiment of the computer-implemented method for providing a vascular image data record.

In a further embodiment of the computer-implemented method for providing a trained function, in a further act, a temporal training maximum intensity projection may be determined based on the plurality of training projection X-ray images. Further, the input data of the trained function may also be based on the temporal training maximum intensity projection.

Herein, the temporal training maximum intensity projection may be determined similarly to the above-described determination of the temporal maximum intensity projection. The temporal training maximum intensity projection may, for example, include all properties of the temporal maximum intensity projection that was described with respect to the computer-implemented method for providing a vascular image data record and vice versa. For example, the temporal training maximum intensity projection may be a temporal maximum intensity projection.

The fact that the input data of the trained function is also based on the temporal training maximum intensity projection enables the robustness of the generation of the vascular image data record to be improved.

In a third aspect, the present embodiments relate to a providing unit including a computing unit and an interface. Herein, the interface may be embodied to receive a plurality of projection-X-ray images recorded in temporal succession.

Further, the computing unit may be embodied to determine a change image data record in each case based on at least one region of interest of the plurality of projection-X-ray images. In addition, the computing unit may be embodied to generate a vascular image data record based on the change image data record. The interface may further be embodied to provide the vascular image data record.

Such a providing unit may be embodied to carry out the above-described method according to the present embodiments for providing a vascular image data record and the aspects thereof. The providing unit is embodied to carry out this method and the aspects thereof in that the interface and the computing unit are embodied to carry out the corresponding method acts.

The advantages of the suggested providing unit substantially correspond to the advantages of the suggested computer-implemented method for providing a vascular image data record. Features, advantages, or alternative embodiments mentioned herein may also be transferred to the other claimed subject matter and vice versa.

In a fourth aspect, the present embodiments relate to a training unit embodied to carry out the above-described computer-implemented method according to the present embodiments for providing a trained function and the aspects thereof. The training unit also includes a training interface and a training computing unit. The training unit is embodied to carry out this method and the aspects thereof in that the training interface and the training computing unit are embodied to carry out the corresponding method acts.

Herein, the training interface may be embodied to receive a plurality of training projection X-ray images recorded in temporal succession. Further, the training computing unit may be embodied to determine a training change image data record in each case based on at least one training region of interest of the plurality of training projection X-ray images. In addition, the training computing unit may be embodied to generate a comparison vascular image data record based on the training change image data record. Further, the training computing unit may be embodied to generate a training vascular image data record by applying the trained function to input data based on the training change image data record. Further, the training computing unit may be embodied to adjust at least one parameter of the trained function based on a comparison of the comparison vascular image data record and the training vascular image data record. In addition, the training interface may be embodied to provide the trained function.

The advantages of the suggested training unit substantially correspond to the advantages of the suggested computer-implemented method for providing a trained function. Features, advantages, or alternative embodiments mentioned herein may also be transferred to the other claimed subject matter and vice versa.

In a fifth aspect, the present embodiments relate to a medical X-ray device including a suggested providing unit. Herein, the medical X-ray device (e.g., the providing unit) is embodied to carry out a suggested computer-implemented method for providing a vascular image data record. For example, the medical X-ray device may be embodied as a medical C-arm X-ray device and/or computed tomography system. Herein, the medical X-ray device may further be embodied to record and/or to receive and/or to provide the plurality of projection-X-ray images.

The advantages of the suggested medical X-ray device substantially correspond to the advantages of the suggested computer-implemented method for providing a vascular image data record. Features, advantages, or alternative embodiments mentioned herein may also be transferred to the other claimed subject matter and vice versa.

In a sixth aspect, the present embodiments relate to a computer program product with a computer program that may be: loaded directly into a memory of a providing unit, with program sections for carrying out all the acts of the computer-implemented method for providing a vascular image data record when the program sections are executed by the providing unit; and/or loaded directly into a training memory of a training unit, with program sections for carrying out all the acts of the method for providing a trained function and/or one of the aspects thereof when the program sections are executed by the training unit.

In a seventh aspect, the present embodiments relate to a computer-readable storage medium on which: program sections that may be read and executed by a providing unit are stored for carrying out all the acts of the computer-implemented method for providing a vascular image data record when the program sections are executed by the providing unit; and/or program sections that may be read and executed by a training unit are stored for carrying out all the acts of the method for providing a trained function and/or a corresponding aspect when the program sections are executed by the training unit.

In an eighth aspect, the present embodiments relate to a computer program or computer-readable storage medium including a trained function provided by a suggested computer-implemented method or one of the aspects thereof.

An extensively software-based implementation has the advantage that it is also possible to retrofit providing units and/or training units used to date in a simple way via a software update in order to work in the manner according to the present embodiments. In addition to the computer program, a computer program product of this kind may optionally include additional parts such as, for example, documentation and/or additional components, and hardware components, such as, for example, hardware keys (e.g., dongles, etc.) for using the software.

BRIEF DESCRIPTION OF THE DRAWINGS

In different figures, the same reference numbers are used for the same features.

DETAILED DESCRIPTION

Figure 1:
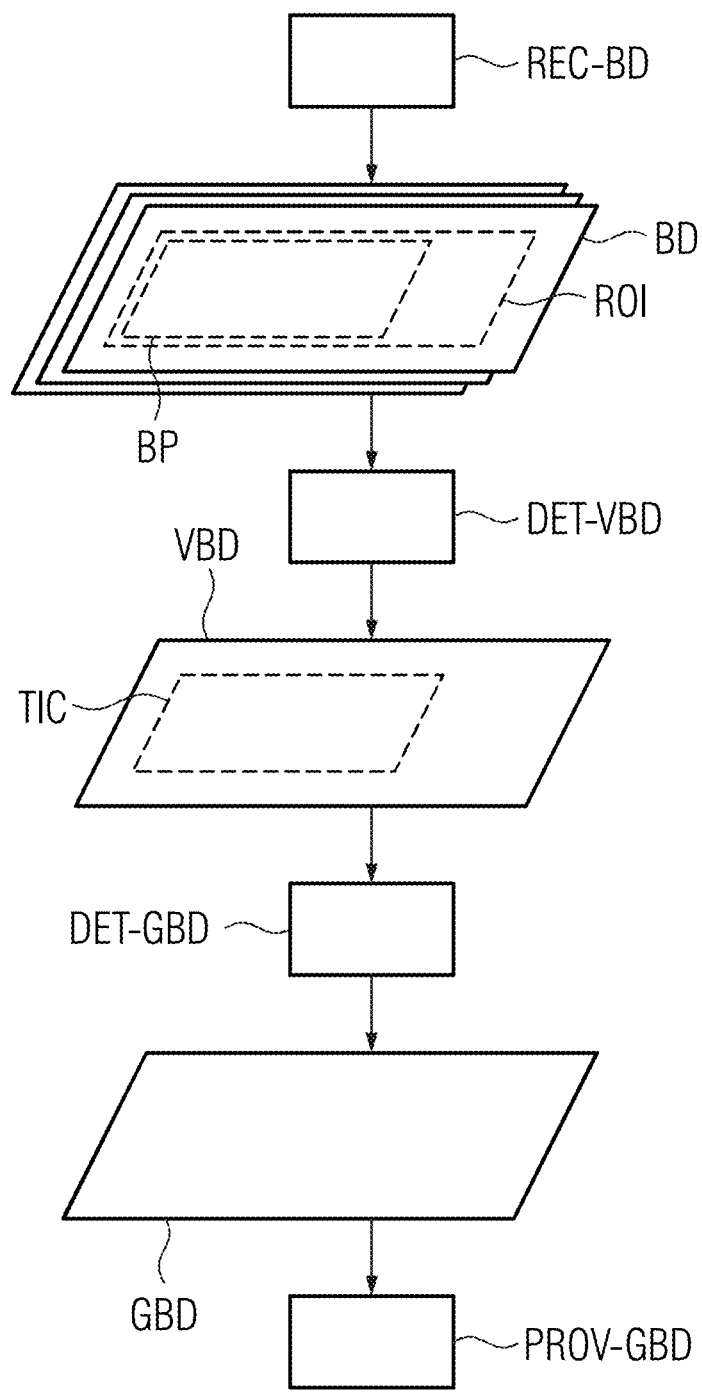
FIGS. 1 to 5 are schematic depictions of different embodiments of a computer-implemented method for providing a vascular image data record.

FIG. 1 is a schematic depiction of an embodiment of a computer-implemented method for providing a vascular image data record. Herein, in a first act a), a plurality of projection-X-ray images BD recorded in temporal succession may be received REC-BD. Herein, the plurality of projection-X-ray images BD may at least partially map a common examination region (e.g., an examination region)

of an examination object. Further, the plurality of projection-X-ray images BD may map a temporal change in the examination region of the examination object. In a second act b), a change image data record VBD may be determined DET-VBD in each case based on at least one region of interest ROI of the plurality of projection-X-ray images BD. Herein, the at least one region of interest ROI may include a plurality of image points BP. Further, the change image data record VBD may in each case include a time-intensity curve TIC for each of the image points BP. In a third act c), the vascular image data record GBD may be generated DET-GBD based on the change image data record VBD. In a fourth act d), the vascular image data record GBD may be provided PROV-GBD.

In addition, the vascular image data record GBD may be generated DET-GBD based on a threshold value with respect to the time-intensity curves TIC of the change image data record VBD.

Figure 2:
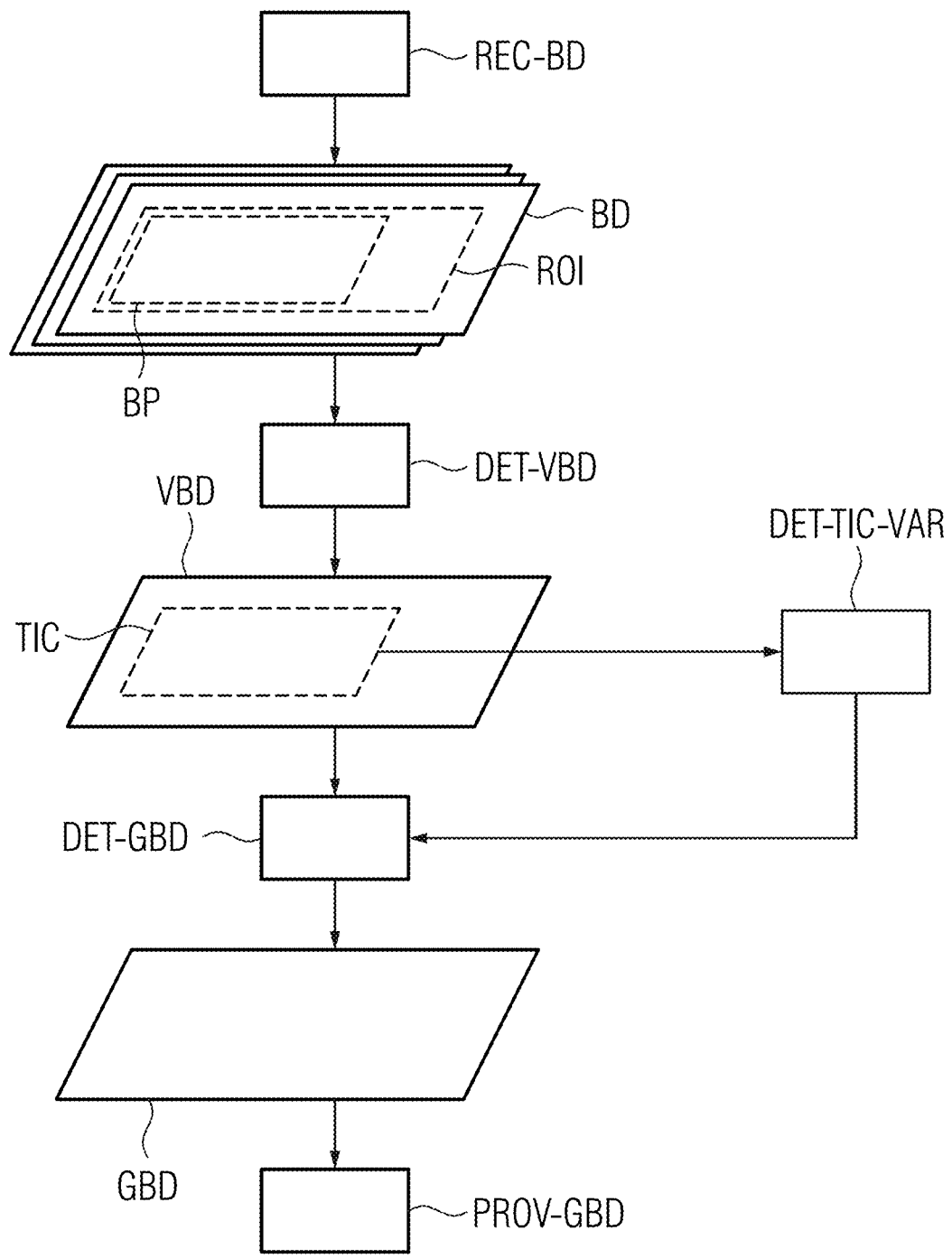

FIG. 2 shows a further embodiment of the suggested computer-implemented method for providing a vascular image data record PROV-GBD. Herein, in each case, a temporal variance may be determined DET-TIC-VAR for each time-intensity curve TIC of the change image data record VBD. Further, the generation of the vascular image data record DET-GBD in act c) may include segmentation of the image points BP of the change image data record VBD based on a comparison of the variance with the threshold value.

Figure 3:
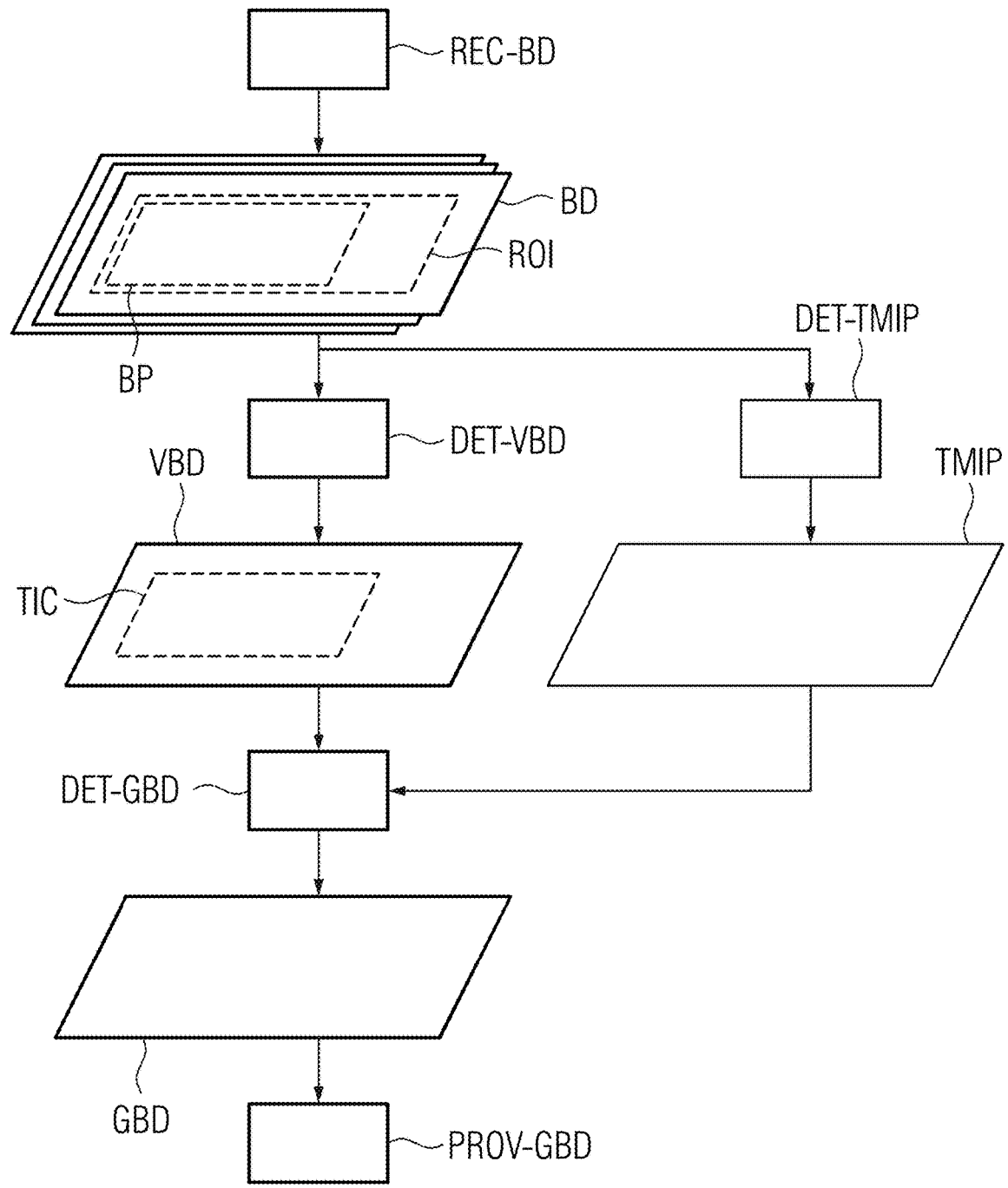

FIG. 3 is a schematic depiction of a further embodiment of the suggested computer-implemented method for providing a vascular image data record PROV-GBD. Herein, a temporal maximum intensity projection TMIP based on the plurality of projection-X-ray images BD may be generated DET-TMIP. Further, the vascular image data record GBD may additionally be generated DET-GBD based on the temporal maximum intensity projection TMIP.

Figure 4:
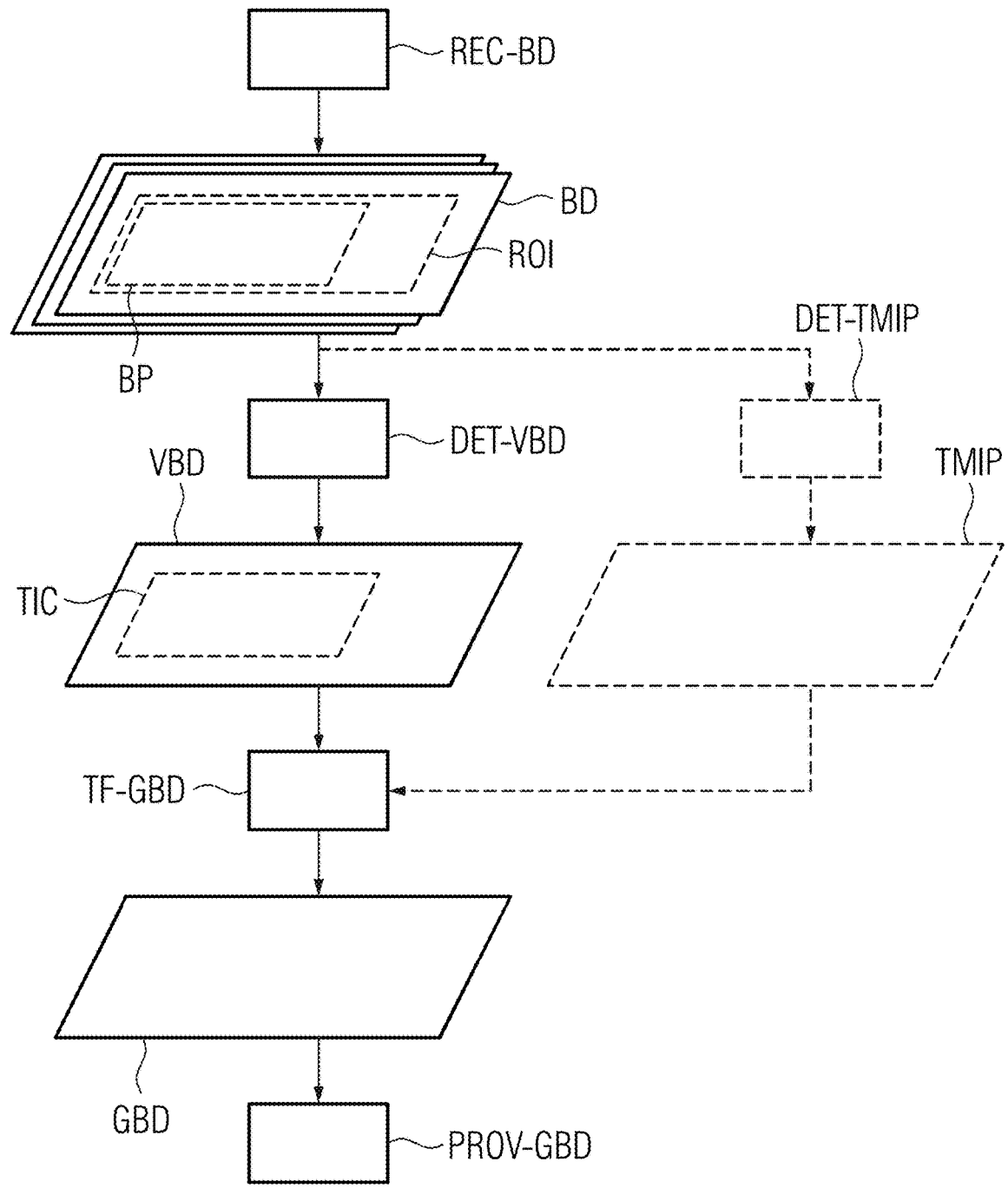

FIG. 4 shows a further embodiment of the suggested computer-implemented method for providing a vascular image data record PROV-GBD. Herein, the generation of the vascular image data record DET-GBD may take place by applying a trained function TF-GBD to input data. Herein, the input data may be based on the change image data record VBD. Further, at least one parameter of the trained function TF-GBD may be based on a comparison of a training vascular image data record and a comparison vascular image data record.

In addition, the input data may also be based on the temporal maximum intensity projection TMIP.

Figure 5:
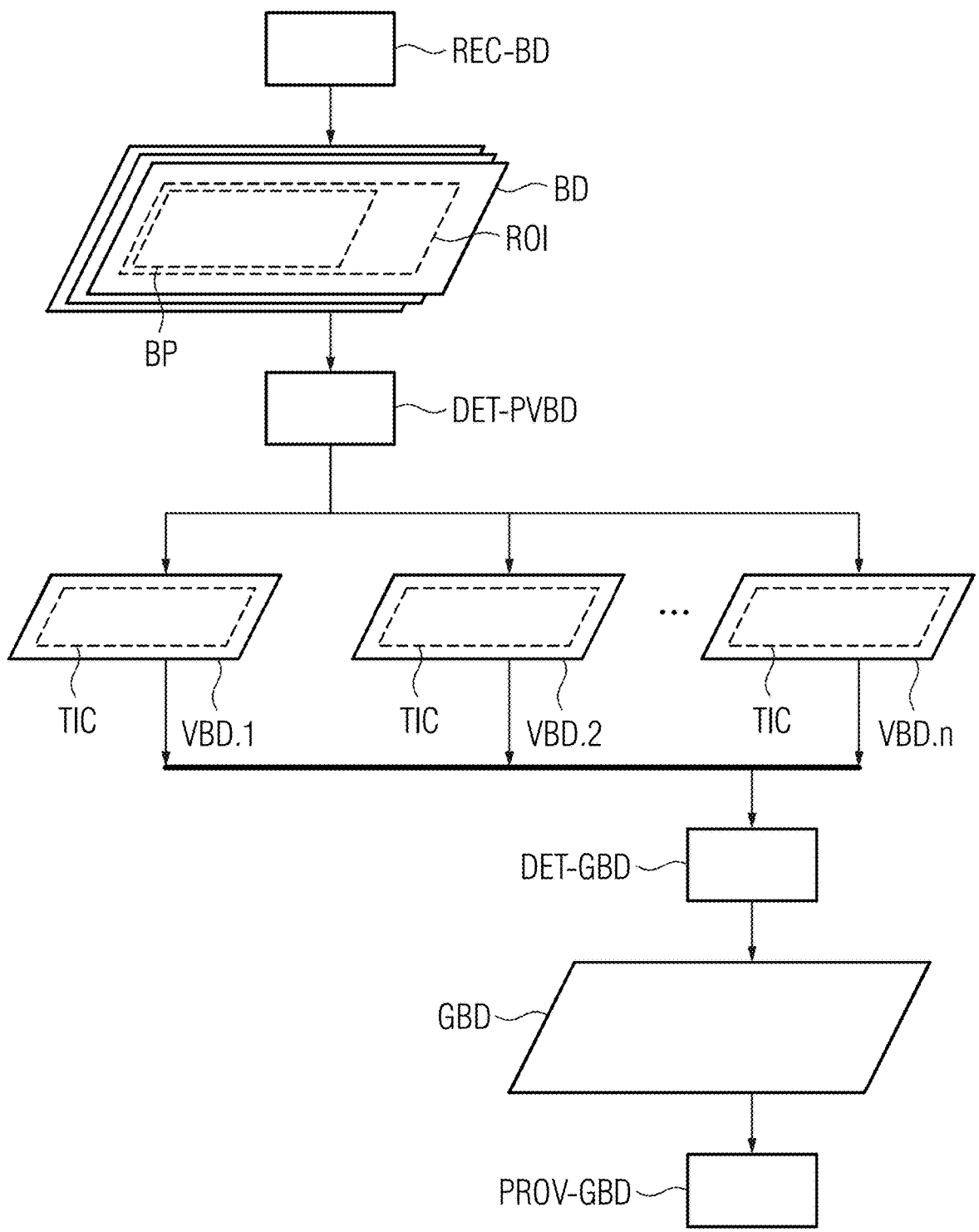

In the embodiment of the computer-implemented method for providing a vascular image data record PROV-GBD schematically depicted in FIG. 5, the plurality of projection-X-ray images BD may map different temporally sequential phases of the temporal change in the examination region of the examination object. Herein, act b) may further include a determination in each case of a phase-change image data record VBD.1, VBD.2 to VBD.n for each of the phases of the temporal change. Further, the phase-change image data records VBD.1, VBD.2 to VBD.n for each of the image points BP may in each case include a time-intensity curve TIC. Herein, the vascular image data record GBD may be completed based on a threshold value with respect to the time-intensity curves TIC of the phase-change image data records VBD.1, VBD.2 to VBD.n.

In one embodiment, the completion of the vascular image data record GBD may take place step-by-step based on the phase-change image data records VBD.1, VBD.2 to VBD.n. Herein, in each act of the completion of the vascular image data record, image points may be classified with reference to the threshold value with respect to the time-intensity curves TIC of the respective phase-change image data record VBD.1, VBD.2 to VBD.n. In one embodiment, the classification of the image points BP may take place based on the image points BP that have already been classified previously.

Figure 6:
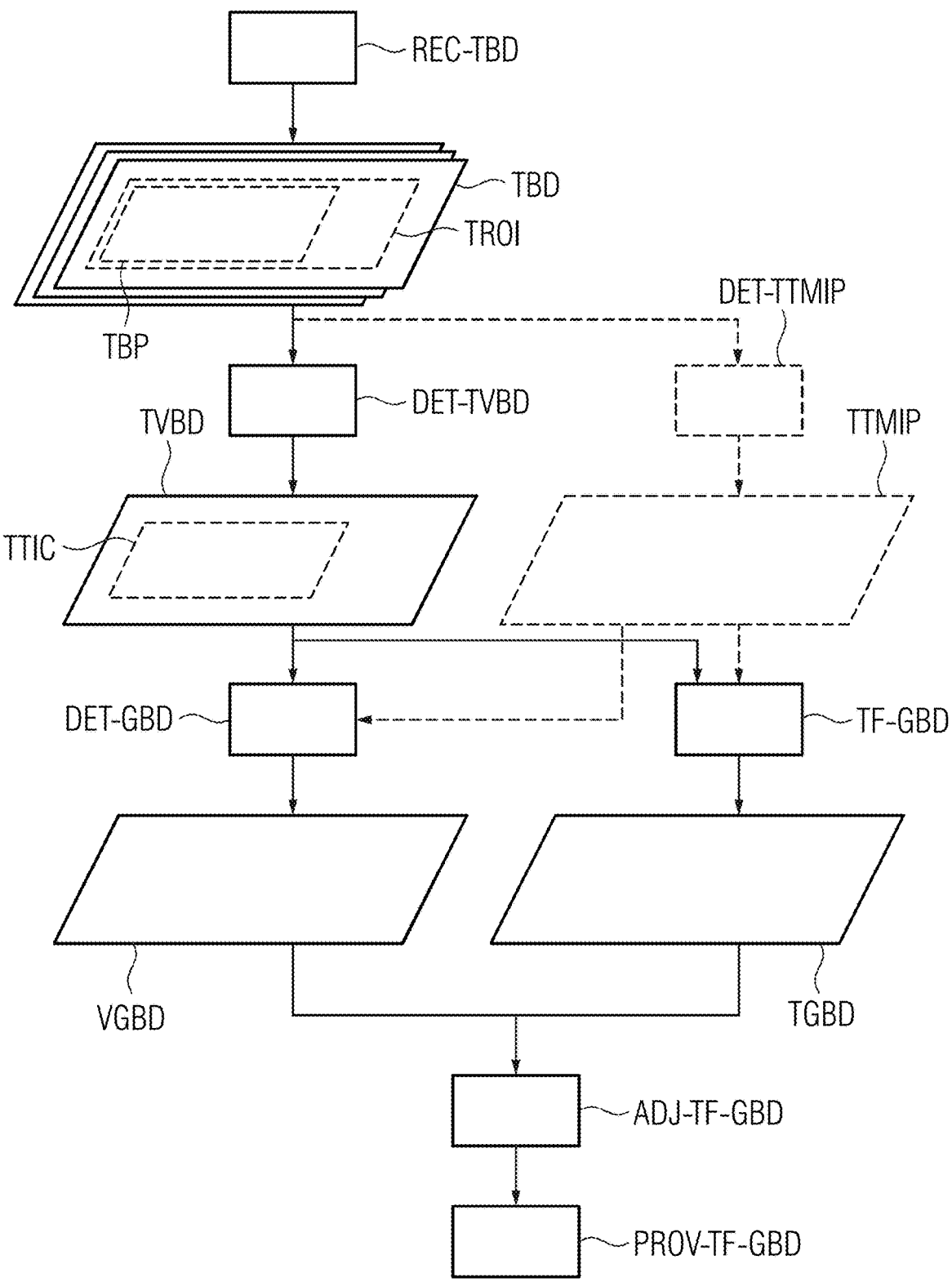
FIG. 6 is a schematic depiction of an embodiment of a suggested computer-implemented method for providing a trained function.
Figure 7:
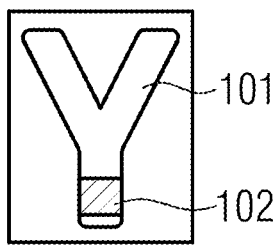
FIGS. 7 to 10 are schematic depictions of a temporal change in an examination region of an examination object.
Figure 8:
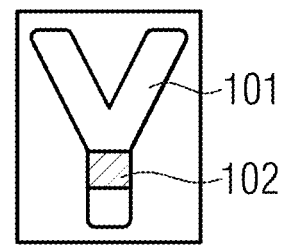
Figure 9:
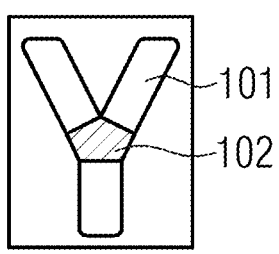
Figure 10:
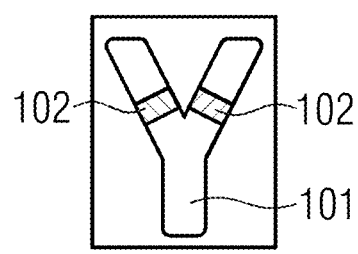

FIG. 6 is a schematic depiction of an embodiment of a computer-implemented method for providing a trained function TF-GBD. Herein, in a first act, a plurality of training projection X-ray images TBD recorded in temporal succession may be received REC-TBD. Herein, the plurality of training projection X-ray images TBD may at least partially map a common examination region of the examination object. Further, the plurality of training projection X-ray images TBD may map a temporal change in the examination region of the examination object. In a second act, a training change image data record TVBD may in each case be determined DET-TVBD based on at least one training region of interest TROI of the plurality of training projection X-ray images TBD. Herein, the at least one training region of interest TROI may include a plurality of training image points TBP. Further, the training change image data record TVBD for each of the training image points TBP may in each case include a training time-intensity curve TTIC. In a third act, a comparison vascular image data record VGBD may be generated DET-GBD based on the training change image data record TVBD. Further, a temporal training maximum intensity projection TTMIP may be determined DET-TTMIP based on the plurality of training projection X-ray images TBD. Herein, the comparison vascular image data record VGBD may additionally be generated DET-GBD based on the temporal training maximum intensity projection TTMIP.

In a fourth act, a training vascular image data record TGBD may be generated by applying the trained function TF-GBD to the input data based on the training change image data record TVBD. Herein, the input data of the trained function TF-GBD may additionally be based on the temporal training maximum intensity projection TTMIP. After this, at least one parameter of the trained function TF-GBD may be adjusted ADJ-TF-GBD based on a comparison of the comparison vascular image data record VGBD and the training vascular image data record TGBD. In a further act, the trained function TF-GBD may be provided PROV-TF-GBD.

FIGS. 7 to 10 are in each case schematic depictions of projection mapping (e.g., a projection X-ray image) of an examination region with a vessel section 101, where the vessel section 101 includes a bifurcation. Herein, the projection mappings mapped in FIGS. 7 to 10 in each case map a time point and/or period of time of the temporal change in the vessel section 101. Herein, the temporal change in the examination region of the examination object (e.g., in the vessel section 101) may be caused by a contrast agent bolus 102. Herein, each of the projection mappings may in each case map a phase of the temporal change in the examination region. In one embodiment, in each case, a phase-change image data record VBD.1 to VBD.n may be determined for each of the phases of the temporal change. Further, the vascular image data record GBD may be completed DET-GBD based on the phase-change image data records VBD.1 to VBD.n.

Figure 11:
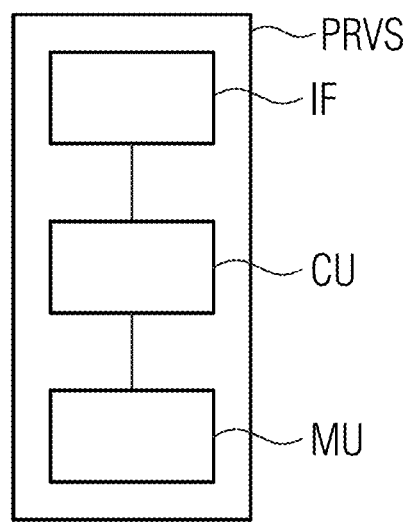
FIG. 11 is a schematic depiction of one embodiment of a providing unit.

FIG. 11 is a schematic depiction of one embodiment of a providing unit PRVS including an interface IF, a computing unit CU, and a memory unit MU. The providing unit PRVS may be embodied to carry out a computer-implemented method for providing a vascular image data record PROV-GBD and the aspects thereof in that the interface IF and the computing unit CU are embodied to carry out the corresponding method acts. Herein, the interface IF may be embodied to receive REC-BD a plurality of projection-X-ray images BD recorded in temporal succession. Further, the computing unit CU may be embodied to determine DET-VBD a change image data record VBD in each case based on at least one region of interest ROI of the plurality of projection-X-ray images BD. In addition, the computing unit CU may be embodied to generate DET-GBD a vascular image data record GBD based on the change image data record VBD. The interface IF may further be embodied to provide PROV-GBD the vascular image data record GBD.

Figure 12:
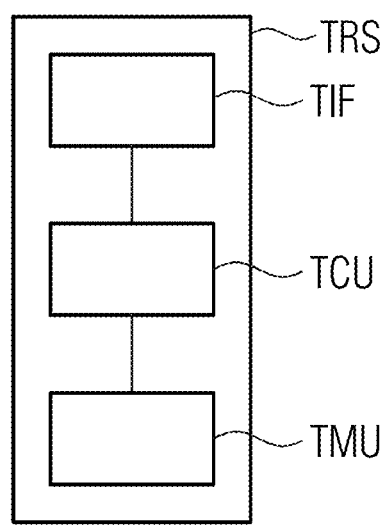
FIG. 12 is a schematic depiction of one embodiment of a training unit.

FIG. 12 is a schematic depiction of one embodiment of a suggested training unit TRS including a training interface TIF, a training computing unit TCU, and a training memory unit TMU. The training unit TRS may be embodied to a carry out a suggested computer-implemented method for providing a trained function PROV-TF-GBD and the aspects thereof in that the training interface TIF and the training computing unit TCU are embodied to carry out the corresponding method steps. Herein, the training interface TIF can be embodied to receive REC-TBD a plurality of training projection X-ray images TBD recorded in temporal succession. Further, the training computing unit TCU may be embodied to determine DET-TVBD a training change image data record TVBD in each case based on at least one training region of interest TROI of the plurality of training projection X-ray images TBD. In addition, the training computing unit TCU may be embodied to generate DET-GBD a comparison vascular image data record VGBD. Further, the training computing unit TCU may be embodied to generate a training vascular image data record TGBD by applying the trained function TF-GBD to input data based on the training change image data record TVBD. Further, the training computing unit TCU may be embodied to adjust ADJ-TF-GBD at least one parameter of the trained function TF-GBD based on a comparison of the comparison vascular image data record VGBD and the training vascular image data record TGBD. In addition, the training interface TIF may be embodied to provide the trained function PROV-TF-GBD.

The providing unit PRVS and/or the training unit TRS may, for example, be a computer, a microcontroller, or an integrated circuit. Alternatively, the providing unit PRVS and/or the training unit TRS may be a real or virtual group of computers (e.g., an English technical term for a real group is "cluster", an English technical term for a virtual group is "cloud"). The providing unit PRVS and/or the training unit TRS may also be embodied as a virtual system that is executed on a real computer or a real or virtual group of computers (e.g., virtualization).

An interface IF and/or a training interface TIF may be a hardware or software interface (e.g., PCI Bus, USB, or Firewire). A computing unit CU and/or a training computing unit TCU may include hardware elements or software elements (e.g., a microprocessor or a field programmable gate array (FPGA). A memory unit MU and/or a training memory unit TMU may be implemented as a non-permanent working memory (e.g., random access memory (RAM)) or as permanent mass storage (e.g., hard disk, USB stick, SD card, solid state disk).

The interface IF and/or the training interface TIF may, for example, include a plurality of subinterfaces that carry out the different acts of the respective methods. In other words, the interface IF and/or the training interface TIF may also be understood to be a multiplicity of interfaces IF or a multiplicity of training interfaces TIF. The computing unit CU and/or the training computing unit TCU may, for example, include a plurality of sub-computing units that carry out the different acts of the respective method. In other words, the computing unit CU and/or the training computing unit TCU may also be understood to be a multiplicity of computing units CU or a multiplicity of training computing units TCU.

Figure 13:
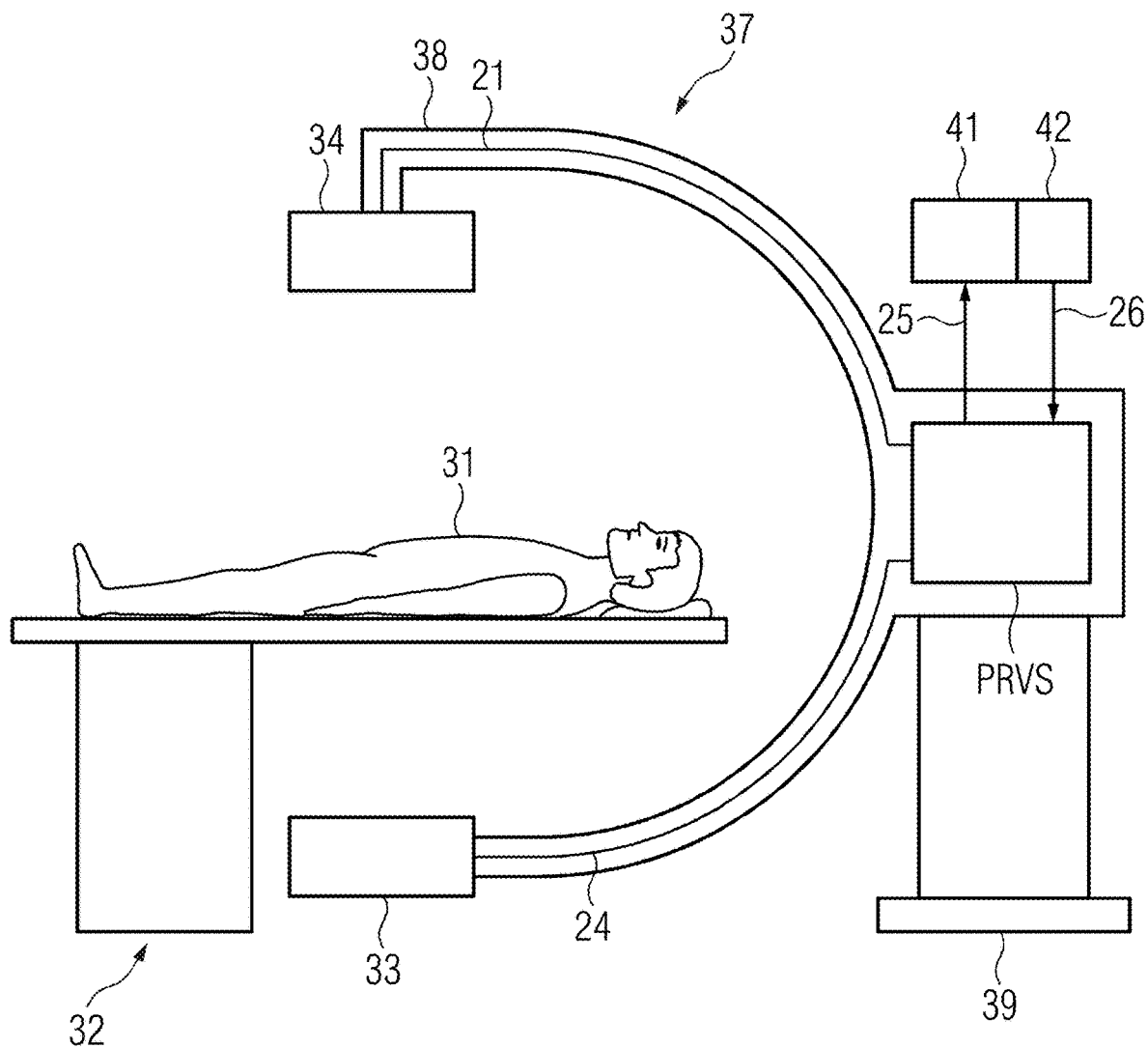
FIG. 13 is a schematic depiction of one embodiment of a medical C-arm X-ray device.

FIG. 13 is a schematic depiction of one embodiment of a medical C-arm X-ray device as an example of a suggested medical imaging device 37. Herein, the medical C-arm X-ray device 37 may include a suggested providing unit PRVS for providing a vascular image data record PROV-GBD. Herein, the medical imaging device 37 (e.g., the suggested providing unit PRVS) is embodied to carry out a suggested computer-implemented method for providing a vascular image data record PROV-GBD.

Herein, the medical C-arm X-ray device 37 also includes a detector unit 34 and an X-ray source 33. In order to record the plurality of projection-X-ray images BD in temporal succession, the arm 38 of the C-arm X-ray device 37 may be mounted movably about one or more axes. Further, the medical C-arm X-ray device 37 may include a movement apparatus 39 that enables movement of the C-arm X-ray device 37 in space.

In order to record the plurality of projection-X-ray images BD from an examination region to be mapped of an examination object 31 arranged on a patient supporting device 32, the providing unit PRVS may send a signal 24 to the X-ray source 33. Following this, the X-ray source 33 may transmit an X-ray beam (e.g., a cone beam and/or fan beam and/or parallel beam). On the impact of the X-ray beam, after interaction with the region of the examination object 31 to be mapped on a surface of the detector unit 34, the detector unit 34 may send a signal 21 to the providing unit PRVS. The providing unit PRVS may, for example, receive REC-BD the plurality of projection-X-ray images BD by the signal 21.

Further, the medical C-arm X-ray device 37 may include an input unit 42 (e.g., a keyboard, and/or a depicting unit 41, such as a monitor and/or a display). The input unit 42 may be integrated in the depicting unit 41 (e.g., in the case of a capacitive input display). Herein, an input of an operator at the input unit 42 may enable control of the medical C-arm X-ray device 37 (e.g., the suggested computer-implemented method for providing a vascular image data record PROV-GBD). For this, the input unit 42 may, for example, send a signal 26 to the providing unit PRVS.

Further, the depicting unit 41 may be embodied to display information and/or graphic depictions of information of the medical imaging devices 37 and/or the providing unit PRVS and/or further components. For this, the providing unit PRVS may, for example, send a signal 25 to the depicting unit 41. For example, the depicting unit 41 may be embodied to display a graphical depiction of the plurality of projection-X-ray images BD and/or the change image data record VBD and/or the vascular image data record GBD. In one embodiment, a graphical (e.g., color-coded) depiction of the change image data record VBD and/or the vascular image data record GBD may be displayed on the depicting unit 41. Further, the graphical depiction of the change image data record VBD and/or the vascular image data record GBD may include a superimposition (e.g., a weighted superimposition) with the projection-X-ray images BD and/or further projection-X-ray images from the examination region of the examination object 31.

The schematic depictions in the described figures are not in any scale or size ratio.

The methods described in detail above and the depicted apparatuses are only exemplary embodiments that may be modified by the person skilled in the art in the most diverse manner without departing from the scope of the invention. Further, the use of the indefinite "a" or "an" does not preclude the possibility that the features in question may also be present on a multiple basis. Similarly, the terms "unit" and "element" do not preclude the possibility that the components in question consist of a plurality of interacting partial components, which may optionally also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for providing a vascular image data record, the computer-implemented method comprising:
  receiving a plurality of projection-X-ray images recorded in temporal succession, wherein the plurality of projection-X-ray images at least partially map a common examination region of an examination object, and wherein the plurality of projection-X-ray images map a temporal change in the common examination region of the examination object;
  determining a change image data record in each case based on at least one region of interest of the plurality of projection-X-ray images, wherein the at least one region of interest comprises a plurality of image points, and wherein the change image data record in each case includes a time-intensity curve for each image point of the plurality of image points;
  generating the vascular image data record based on the change image data record, wherein the vascular image data record is generated based on a threshold value with respect to the time-intensity curves of the change image data record;
  determining, for each of the time-intensity curves of the change image data record, a temporal variance, wherein generating the vascular image data record comprises segmenting the plurality of image points based on a comparison of the temporal variance with the threshold value; and
  providing the vascular image data record.

2. The computer-implemented method of claim 1, further comprising generating a temporal maximum intensity projection based on the plurality of projection-X-ray images, wherein the generating of the vascular image data record is further based on the temporal maximum intensity projection.

3. The computer-implemented method of claim 2, wherein generating the vascular image data record comprises applying a trained function to input data,
  wherein the input data is based on the change image data record, and
  wherein at least one parameter of the trained function is based on a comparison of a training vascular image data record and a comparison vascular image data record.

4. The computer-implemented method of claim 3, wherein the input data is further based on the temporal maximum intensity projection.

5. The computer-implemented method of claim 1, wherein the plurality of projection-X-ray images map different temporally sequential phases of the temporal change in the common examination region of the examination object,
  wherein determining the change image data record comprises determining in each case a phase-change image data record for each of the phases of the temporal change, and
  wherein the vascular image data record is generated based on the phase-change image data records.

6. The computer-implemented method of claim 5, wherein each of the phase-change image data records includes a time-intensity curve for each image point of the plurality of image points, and
  wherein the vascular image data record is completed based on a threshold value with respect to the time-intensity curves of the phase-change image data records.

7. The computer-implemented method of claim 6, wherein the completion of the vascular image data record takes place step-by-step based on the phase-change image data records,
  wherein in each step of the completion of the vascular image data record, image points are classified with reference to the threshold value with respect to the time-intensity curves of the respective phase-change image data record, and
  wherein the classification of the image points takes place performed based on the image points that have already been classified previously.

8. The computer-implemented method of claim 1, wherein the temporal change in the common examination region of the examination object is caused by a contrast agent bolus.

9. A computer-implemented method for providing a trained function, the computer-implemented method comprising:
  receiving a plurality of training projection-X-ray images recorded in temporal succession, wherein the plurality of training projection-X-ray images at least partially map a common examination region of an examination object, and wherein the plurality of training projection-X-ray images map a temporal change in the common examination region of the examination object;
  determining a training change image data record in each case based on at least one training region of interest of the plurality of training projection-X-ray images, wherein the at least one training region of interest comprises a plurality of training image points, and wherein the training change image data record in each case includes a training time-intensity curve for each training image point of the plurality of training image points;

generating a comparison vascular image data record based on the training change image data record;

generating a training vascular image data record, the generating of the training vascular image data record comprising applying a trained function to input data, wherein the input data is based on the training change image data record;

adjusting at least one parameter of the trained function based on a comparison of the comparison vascular image data record and the training vascular image data record; and providing the trained function.

10. The computer-implemented method of claim 9, further comprising determining a temporal training maximum intensity projection based on the plurality of training projection-X-ray images, wherein the input data is also based on the temporal training maximum intensity projection.

11. A providing unit for providing a vascular image data record, the providing unit comprising:

a processor configured to:

receive a plurality of projection-X-ray images recorded in temporal succession, wherein the plurality of projection-X-ray images at least partially map a common examination region of an examination object, and wherein the plurality of projection-X-ray images map a temporal change in the common examination region of the examination object;

determine a change image data record in each case based on at least one region of interest of the plurality of projection-X-ray images, wherein the at least one region of interest comprises a plurality of image points, and wherein the change image data record in each case includes a time-intensity curve for each image point of the plurality of image points;

generate the vascular image data record based on the change image data record, wherein the vascular image data record is generated based on a threshold value with respect to the time-intensity curves of the change image data record;

determine, for each of the time-intensity curves of the change image data record, a temporal variance, wherein to generate the vascular image data record the processor is further configured to segment the plurality of image points based on a comparison of the variance with the threshold value; and provide the vascular image data record.

12. A training unit for providing a trained function, the training unit comprising:

a processor configured to:

receive a plurality of training projection-X-ray images recorded in temporal succession, wherein the plurality of training projection-X-ray images at least partially map a common examination region of an examination object, and wherein the plurality of training projection-X-ray images map a temporal change in the common examination region of the examination object;

determine a training change image data record in each case based on at least one training region of interest of the plurality of training projection-X-ray images, wherein the at least one training region of interest comprises a plurality of training image points, and wherein the training change image data record in each case includes a training time-intensity curve for each training image point of the plurality of training image points;

generate a comparison vascular image data record based on the training change image data record;

generate a training vascular image data record, the generating of the training vascular image data record comprising applying a trained function to input data, wherein the input data is based on the training change image data record;

adjust at least one parameter of the trained function based on a comparison of the comparison vascular image data record and the training vascular image data record; and provide the trained function.

\* \* \* \* \*